United States Patent [19]

Tabaru et al.

[11] Patent Number: 5,356,621
[45] Date of Patent: Oct. 18, 1994

[54] METHOD OF ATTRACTING FLIES

[75] Inventors: Yuichiro Tabaru; Akio Saito, both of Tokyo, Japan

[73] Assignee: Sankyo Company, Limited, Tokyo, Japan

[21] Appl. No.: 971,983

[22] Filed: Feb. 10, 1993

[30] Foreign Application Priority Data

Aug. 30, 1990 [JP] Japan .................. 2-229327

[51] Int. Cl.$^5$ ............ A01N 25/02; A01N 57/16; A01N 37/00; A61K 35/78
[52] U.S. Cl. .................. 424/84; 424/195.1; 514/87; 514/89; 514/100; 514/120; 514/129; 514/530; 514/136; 514/622
[58] Field of Search .......... 424/84, 195.1; 514/87, 514/89, 100, 120, 129, 530, 531, 622, 136

[56] References Cited

U.S. PATENT DOCUMENTS

| 4,201,776 | 5/1980 | Naito et al. | 424/195 |
| 4,684,740 | 8/1987 | Higuchi et al. | 549/464 |

FOREIGN PATENT DOCUMENTS 54-5072  1/1979  Japan .
2-180804  7/1990  Japan .

OTHER PUBLICATIONS

Mano et al, Production of Fungiude for Food, Patent Abstracts of Japan, vol. 11, No. 159, May 22, 1987.
Sakai, Healthful Food Containing Bamboo Extract, Patent Abstracts of Japan, vol. 6, No. 110, Jun. 22, 1982.
Eto, Collection of Essence From Bamboos, Patent Abstracts of Japan, vol. 16, No. 244, Jun.4, 1992.
Sadano, Bamboo Essence-Containing Food, Production Thereof and Container for Adding Bamboo Essence, Patent Abs. of Japan, vol. 14, No. 403 Aug. 31, 1990.
Suzuki et al, Production of Powder Antimicrobial Agent, Patent Abs. of Japan, vol. 17, No. 30, Jan. 20, 1993.
Kawai, Beatifying Agent of Teeth, Patent Abs. of Japan, vol. 16, No. 298, Jul. 2, 1992.

*Primary Examiner*—Richard L. Raymond
*Assistant Examiner*—Deborah Lambkin
*Attorney, Agent, or Firm*—Frishauf, Holtz, Goodman & Woodward

[57] ABSTRACT

A method of attracting flies of the Muscidae or Muscinae families comprising providing in a locus where the flies exist a fly attractant composition which contains as an active ingredient a composition extracted from a bamboo with an extractive solvent such as water or $C_1$-$C_4$ alcohol.

17 Claims, 8 Drawing Sheets

Retention Time (min)

FIG. 4

Retention Time (min)

Retention Time (min)

METHOD OF ATTRACTING FLIES

TECHNICAL FIELD

This invention relates to a fly attractant containing as an active ingredient composition extracted from a bamboo with an extractive solvent or extract squeezed from a bamboo.

TECHNICAL BACKGROUND

Flies breed in large flocks in poultry houses, pig houses, cow houses and refuse disposal stations, and they not only affect the working efficiency at the spots of breeding but also are becoming a public nuisance in the residential area in the neighborhood. For controlling of these flies, pyrethroids, organophosforus and carbamates are widely used for adult and larval control, and insect growth regulators are widely used for larval control. However, the efficacy of such methods are notably reduced recently due to the development of resistance to the flies to these agents and to the development of large-scale facilities. Particularly, control of Fannia spp. in deep-bed poultry houses are extremely difficult. The reasons are that the larvae of Fannia are not very sensitive to various chemicals and that it is not only difficult to spray to the breeding spots which is located just under the cages, but also the chemical solutions do not fully penetrate into the manure. Consequently, adult control is widely employed for the Fannia. However, such technique is not fully effective, since sometimes it is required to expend work for removing the flies from the poultry houses. Meanwhile, a Paint On Baits method (attractant-incorporated insecticide for residual spray method) is proposed to spray an insecticide to which a syrup or sugar having an attracting action is incorporated, to ceilings where the adults of Fannia rest during the night. This method is utilized to increase the efficiency (e.g. "Chikusan no Kenkyu (Study on Livestock Industry)", 42, 745–748, 846–850 (1988): "Seikatsu to Kankyo (Living and Environment)", 36 (No. 8), 106–113 (1991)). The attractants disclosed in these literatures failed to yield satisfactory results, since they can exhibit a small effect of attracting the flies to the sprayed spots, although they may show an increased effectiveness only when the flies happen to rest on the sprayed surface.

There are also various kinds of known fly catching techniques using, for example, a fly attracting trap, a fly ribbon and flypaper. However, few of the attractants used in these methods such as syrups and sweeteners can yield satisfactory results.

DISCLOSURE OF THE INVENTION

The present inventors made years of intensive studies to find that a composition extracted from a bamboo with an extractive solvent or extract squeezed from a bamboo can exhibit an excellent effect of attracting flies and that it can be an excellent novel attractant when used for fly control resorting to the attractant-incorporated insecticide for residual spray method or to a fly attracting trap and the like, and they accomplished this invention.

CONSTITUTION OF THE INVENTION

The fly attractant of the present invention contains a composition extracted from a bamboo with an extractive solvent or extract squeezed from a bamboo.

The bamboo employable according to the present invention can be those belonging to Gramineae or Bambusoideae, including, for example, *Phyllostachys heterocycla, Phyllostachys nigra, Phyllostachys bambusoides* and ground bamboo (particularly a shoot thereof), preferably a shoot of *Phyllostachys heterocycla* and *Phyllostachys bambusoides*.

The solvent employable for extracting from a bamboo includes hydrocarbons such as hexane, benzene, toluene and xylene; ethers such as diethyl ether, tetrahydrofuran, dioxane and 1,2-dimethoxyethane; esters such as methyl acetate and ethyl acetate: alcohols such as methanol. ethanol, propanol and butanol; halogenated hydrocarbons such as methylene chloride, chloroform and carbon tetrachloride; amides such as dimethylformamide and dimethylacetamide; nitriles such as acetonitrile; sulfoxides such as dimethyl sulfoxide; and water or mixtures of such organic solvents with water, preferably ethers, aqueous ethers, alcohols, aqueous alcohols and water, more preferably alcohols and water, and particularly preferably methanol and ethanol.

The fly to be attracted may not particularly be limited so long as they belong to Muscidae or Muscinae of Diptera and include, for example, *Musca domestica, Fannia canicularis* and *Muscina stabulans*.

The composition extracted from a bamboo of the present invention can readily be prepared in the following manner. For example, a bamboo (preferably a bamboo shoot whose sheath is removed) is finely chopped, an extractive solvent is added thereto to carry out extraction at 0° to 200° C. (preferably at room temperature to 150° C.) for 30 minutes to 48 hours (preferably 1 to 24 hours) and then the extract solution is concentrated or the extractive solvent is evaporated from the extract solution to obtain the composition. Otherwise, the bamboo extract can be obtained by finely chopping or compressing a bamboo (preferably a bamboo shoot whose sheath is removed) to squeeze out a juice therefrom.

EFFECT OF THE INVENTION

The composition extracted from a bamboo with an extractive solvent or extract squeezed from a bamboo shows an excellent effect of attracting flies and can be used for control of flies resorting to the attractant-incorporated insecticide for residual spray method or to a fly attracting trap and the like. Fly attracting activities were tested for composition extracted from a bamboo shoot with an extractive solvent, as described below.

TEST EXAMPLE 1

Fly attracting activity (1) Preparation of attractant composition

An attractant composition was prepared by mixing 10 ml (active ingredient: 100 mg) of a 1% solution of Azamethiophos (insecticide), 10 g of a sugar and 10 ml of each extract solution obtained in Preparation Examples 1 to 3.

(2) Effectiveness of attracting flies

Each 1 ml of the attractant composition was dropped to filter papers No. 2 having a diameter of 9 cm, and the thus treated filter papers were placed on dishes having a diameter of 9 cm and dried. These dishes were arranged on tables in a poultry farm at 30 cm intervals. After 60 minutes, the number of flies attracted to the dishes were recorded. The results are shown in Table 1.

TABLE 1

| No. | Bamboo Shoot Extract | Number of flies attracted |
|---|---|---|
| 1 | Extract with Ethanol | 45*) |
| 2 | Extract with Methanol | 29 |
| 3 | Extract with Water | 16 |
| 4 | None (Mixture of an insecticide and sugar) | 3 |

*)*Musca domestica*: 2; *Eannia canicularis*: 29; *Muscina stabulans*: 13; miscellaneous: 1

As demonstrated by Test Example 1, the bamboo shoot extracts showed excellent effect of attracting various kinds of flies.

Industrial Utilizability

As described above, a composition extracted from a bamboo with extractive solvents or an extract squeezed from a bamboo can show an excellent effect of attracting flies and can be utilized for the fly control resorting to the attractant-incorporated insecticide for residual spray method or to a fly attracting trap and the like.

The composition or extract of the invention is preferably allowed to have an appropriate dosage form for insecticidal preparations or incorporated into a system by the methods well known in the art.

For example, when the composition or extract from a bamboo is employed in the attractant-incorporated insecticide for residual spray method, a wettable powder or an emulsifiable concentrate of organophosphate insecticides such as propetamphos, azamethipos, chloropyrifos-methyl, diazinon, trichlorfon and fenitrothion; pyrethroids such as allethrin, permethrin, chrysron and etofenprox; and carbamate insecticides such as carbaryl, propoxur and 2-s-butylphenyl N-methylcarbamate (BPMC) is diluted arbitrarily with water, and then the composition or extract of the present invention is added thereto to provide a spray. The composition of the invention (extract solution) is used in an amount of 0.01 to 10 w/w % (preferably 0.05 to 1 w/w %) based on the diluted insecticide solution (containing about 0.2% by weight of active insecticidal ingredient).

Meanwhile, when the composition or extract from a bamboo is used for controlling method resorting to fly attracting trap, it is preferably allowed to have an appropriate dosage form using adjutants. The adjuvants include, for example, alcohols such as methanol, ethanol, propanol, butanol and octanol, fuel oils, machine oils, paper, sugar, milk, non-fat dry milk, rice bran, wheat bran, corn powder, flour and livestock feed. The composition or extract of the invention is dissolved in such adjuvant, or such adjuvant is impregnated with the composition or extract of the invention to provide a suitable dosage form which is then set in a trap having an appropriate design. The composition of the present invention (extract solution) is used in an amount of 0.05 to 10 (preferably 0.1 to Z) based on the dilute insecticide solution (containing about 0.1% by weight of the active insecticidal ingredient) in terms of weight ratio. Meanwhile, heat, wind, etc. can be utilized for diffusing the attractant ingredient, whereas light or sex pheromone can additionally be used for enhancing the effectiveness of attracting flies.

Further, when the composition or extract of the invention is used in a method resorting to fly ribbons or flypapers, it is admixed with a sticky substance such as a mixture of gum arabic, vinyl chloride emulsion and castor oil, and then, for example, paper boards, synthetic resin plates, plywoods or fiber ropes are immersed in the resulting mixture, or the resulting mixture is sprayed onto such base to provide fly ribbons and the like. The attractant composition can also be sprayed on commercially available fly ribbons.

BEST MODE FOR PRACTICING THE PRESENT INVENTION

Next, the present invention will be described more specifically by way of Preparation Examples and Formulation Examples.

PREPARATION EXAMPLE 1

Preparation of methanol extract solution 250 g of shoots of *Phyllostachys bambusoides* were finely chopped, 500 ml of methanol was added thereto and then the mixture was refluxed with heating for 2 hours. After cooling of the mixture, the insolubles were filtered off and the filtrate was concentrated to 200 ml under reduced pressure. The concentrate was washed with 200 ml of hexane and further concentrated to 100 ml under reduced pressure to obtain a methanol extract solution.

Figure 1:
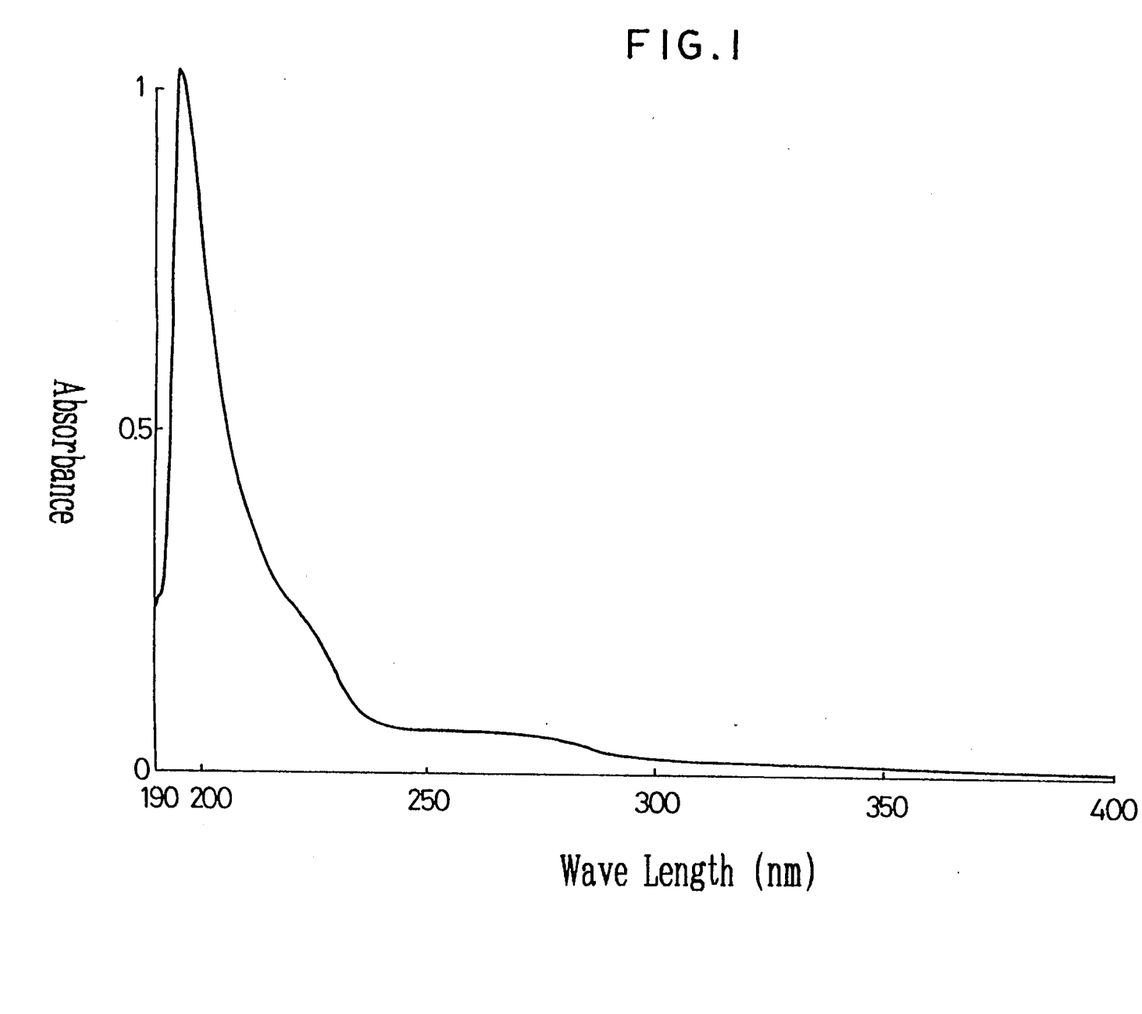
FIG. 1 shows a UV spectrum of the methanol extract solution.
Figure 2:
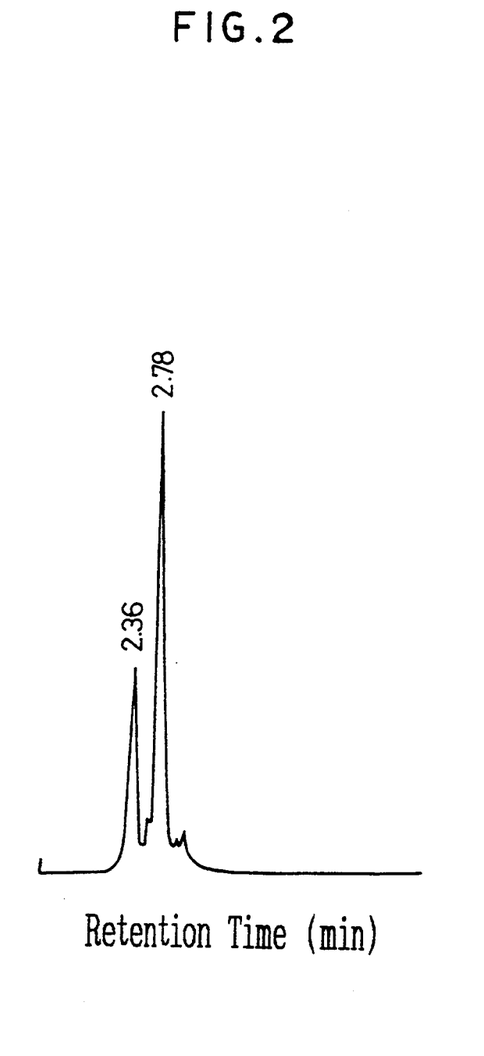
FIG. 2 shows a high-performance liquid chromatogram of the methanol extract solution.

A UV spectrum of a sample prepared by dissolving 1 mg of the thus obtained extract solution in 10 ml of a 50% aqueous ethanol is shown in FIG. 1. Meanwhile, a high-performance liquid chromatogram (column: Inertsil ODS-2, manufactured by G,L Science; eluent: water/acetonitrile=20/80; flow rate: 1 ml/min; detector: 220 nm UV detector) of this extract solution is shown in FIG. 2. Incidentally, the numerals in FIG. 2 are the retention time (minute).

PREPARATION EXAMPLE 2

Preparation of ethanol extract solution 250 g of shoots of *Phyllostachys bambusoides* were finely chopped, 500 ml of ethanol was added thereto and then the mixture was allowed to stand at room temperature overnight.

After the insolubles were filtered off, the filtrate was concentrated to 100 ml under reduced pressure to obtain an ethanol extract solution.

Figure 3:
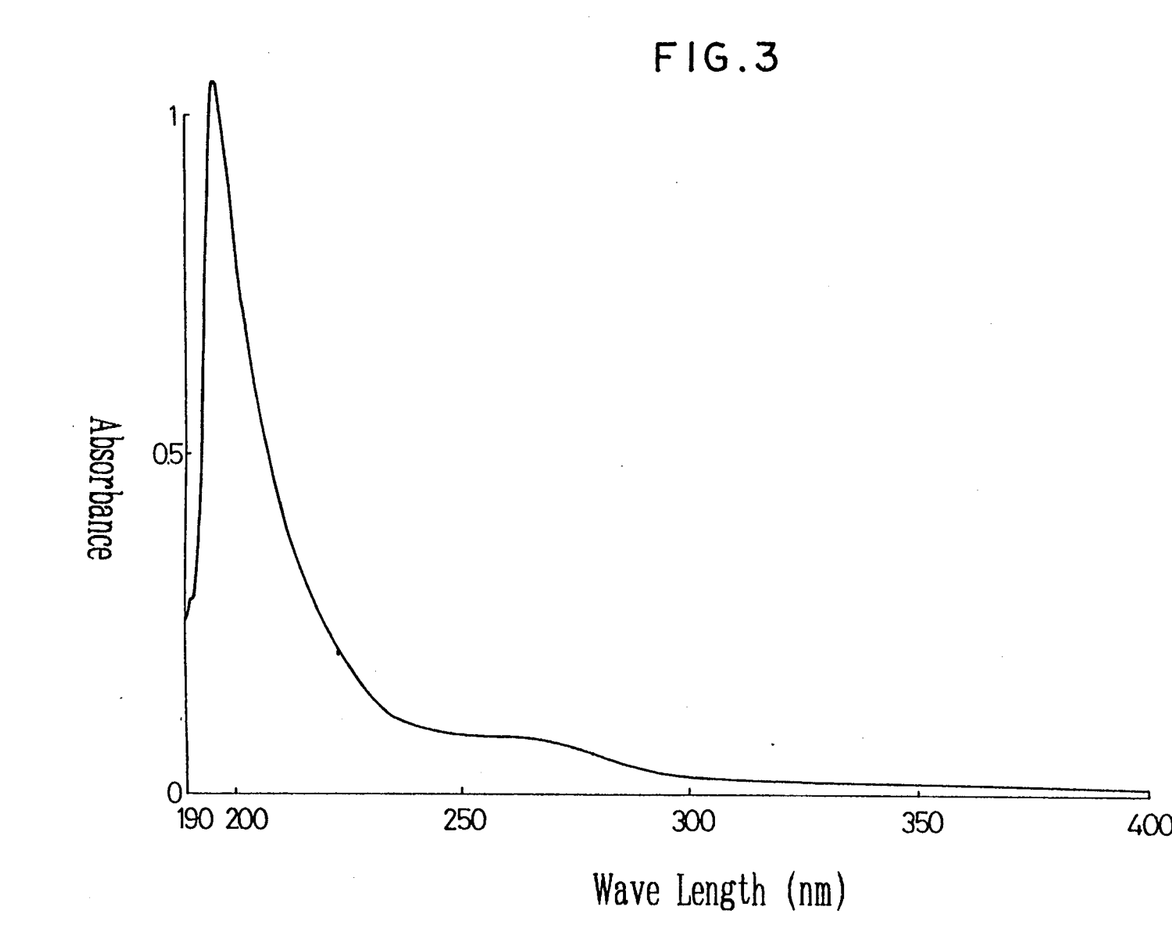
FIG. 3 shows a UV spectrum of the ethanol extract solution.
Figure 4:
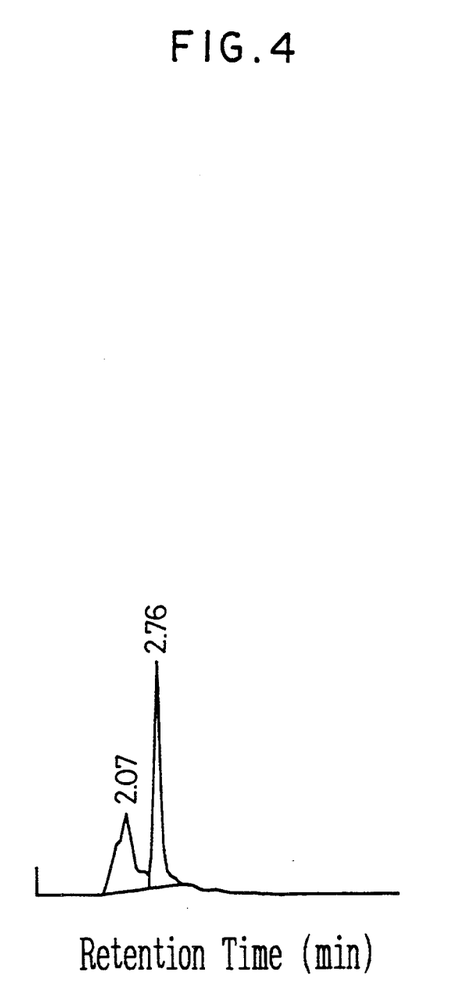
FIG. 4 shows a high-performance liquid chromatogram of the ethanol extract solution.

A UV spectrum of a sample prepared by dissolving 1 mg of the thus obtained extract solution in 10 ml of a 50% aqueous ethanol is shown in FIG. 3. Meanwhile, a high-performance liquid chromatogram (under the same measurement conditions as in the case of methanol extract solution) of this extract solution is shown in FIG. 4. Incidentally, the numerals in FIG. 4 are the retention time (minute).

PREPARATION EXAMPLE 3

Preparation of aqueous extract solution 250 g of shoots of *Phyllostachys bambusoides* were finely chopped, 500 ml of a distilled water were added thereto and then the mixture was heated until about half of the water was distilled off (about 2 hours). After cooling of the residue, the insolubles therein were filtered off to obtain an aqueous extract solution.

Figure 5:
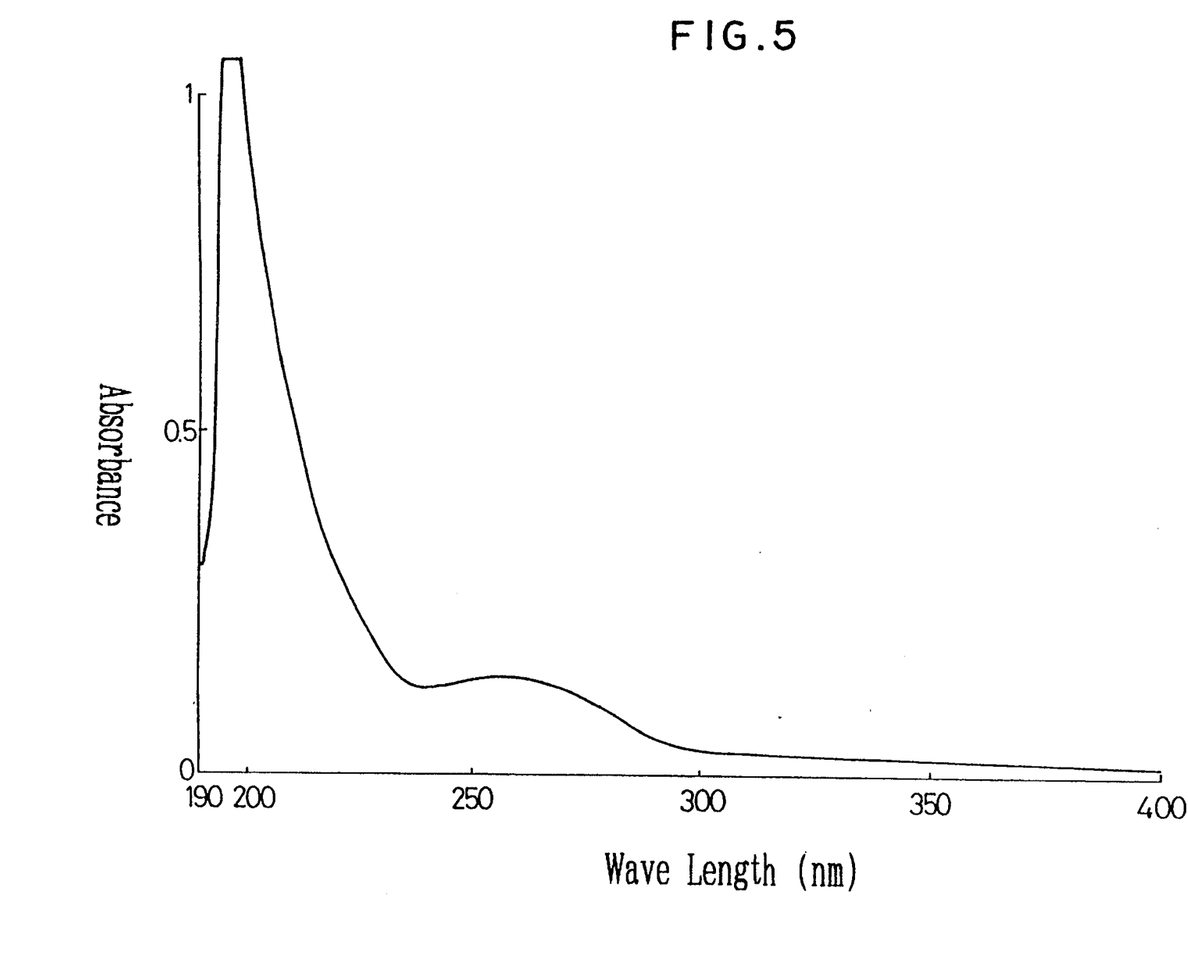
FIG. 5 shows a UV spectrum of the aqueous extract solution.
Figure 6:
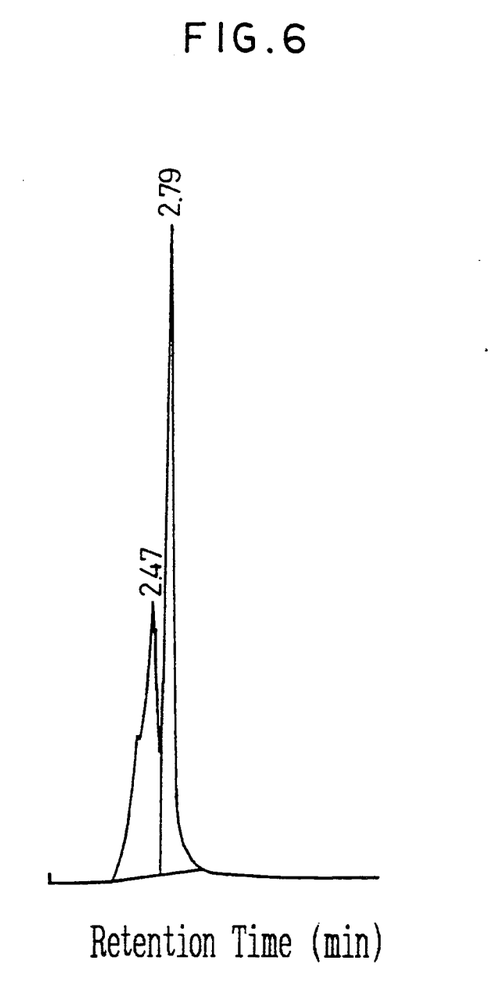
FIG. 6 shows a high-performance liquid chromatogram of the aqueous extract solution.

A UV spectrum of a sample prepared by dissolving 1 mg of the thus obtained extract solution in 10 ml of a 50% aqueous ethanol is shown in FIG. 5. Meanwhile, a high-performance liquid chromatogram (under the same measurement conditions as in the case of methanol extract solution) of this extract solution is shown in FIG. 6. Incidentally, the numerals in FIG. 6 are the retention time (minute).

Figure 7:
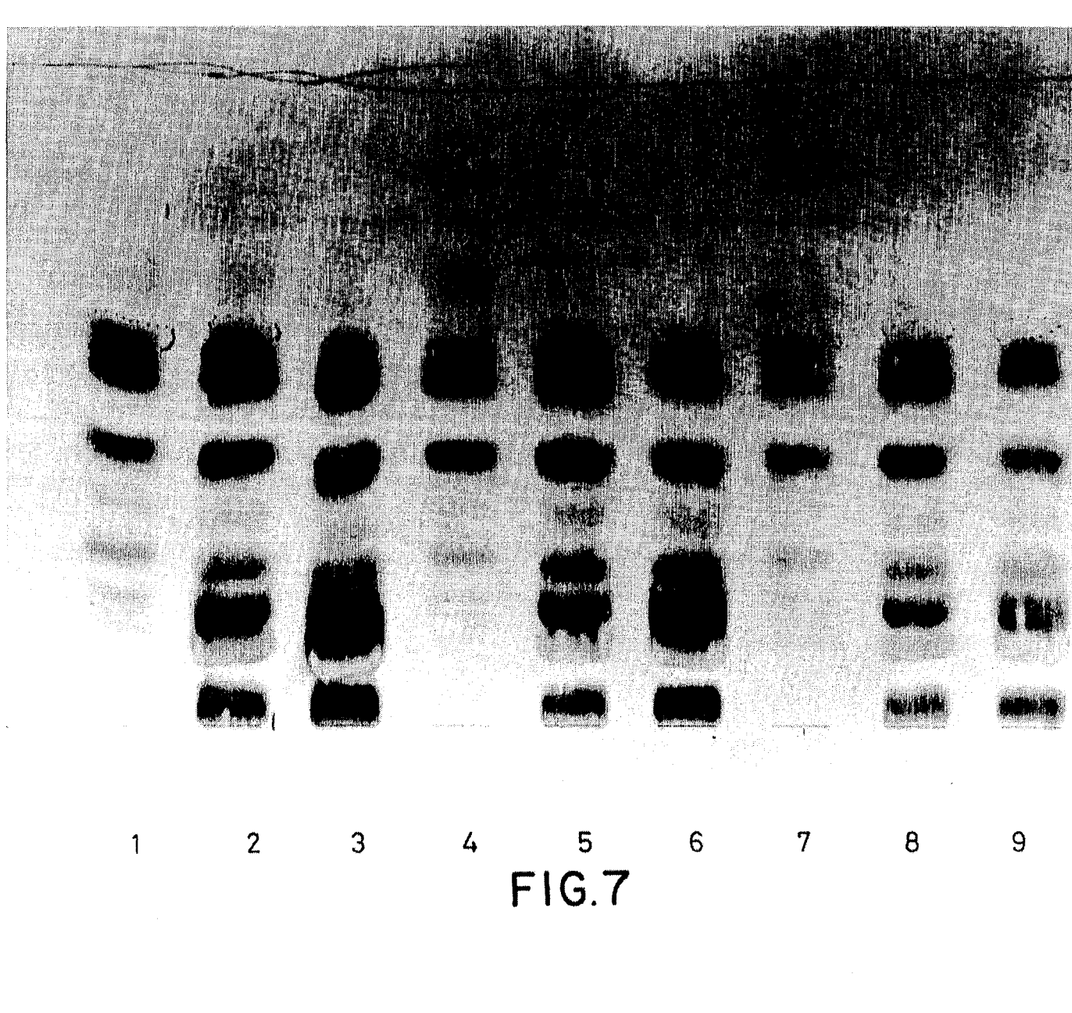
FIG. 7 shows silica gel thin layer chromatograms of the ethanol extract solution, methanol extract solution and aqueous extract solution staining with ninhydrin.
Figure 8:
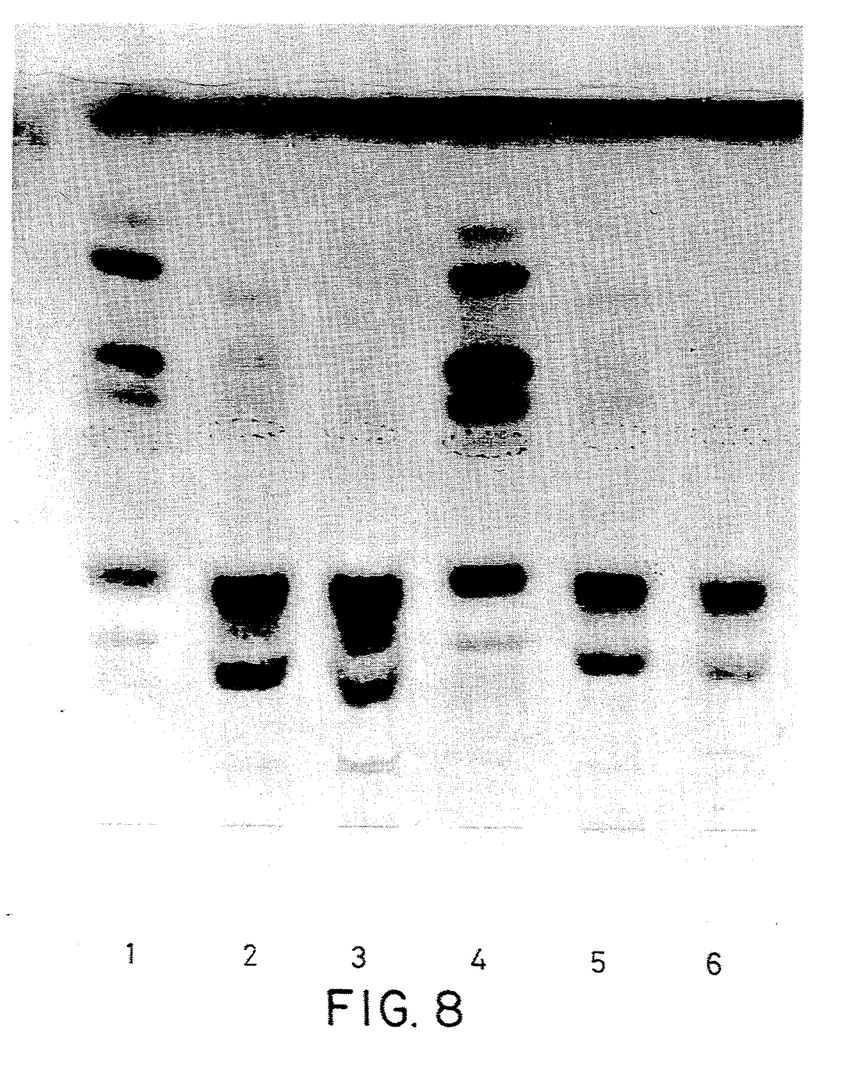
FIG. 8 shows silica gel thin layer chromatograms of the ethanol extract solution, methanol extract solution and aqueous extract solution staining with p-anisaldehyde.

Further, silica gel thin-layer chromatograms (developing solvent: butanol/acetic acid/water=5/1/1) of the extract solutions obtained in Preparation Examples 1 to 3 are shown in FIG. 7 (staining with ninhydrin) and in FIG. 8 (staining with p-anisaldehyde), respectively. Incidentally, in FIG. 7, the numerals 1, 4 and 7 are chromatograms of ethanol extract solutions having different concentrations, 2, 5 and 8 are those of methanol extract solutions having different concentrations and 3, 6 and 9 are those of aqueous extract solutions having different concentrations; while in FIG. 8, the numerals 1 and 4 are chromatograms of ethanol extract solutions having different concentrations, 2 and 5 are those of methanol extract solutions having different concentrations and 3 and 6 are those of aqueous extract solutions having different concentrations. The dotted spots in FIGS. 7 and 8 are those having UV absorption band (254 nm).

FORMULATION EXAMPLE 1

Spray 100 g of a wettable powder containing 50% of Propentaphos manufactured by Sankyo Co., Ltd. were diluted 300-fold with water, and 75 g of the methanol extract solution obtained in Preparation Example 1 were added thereto and dispersed homogeneously therein to provide a spray containing 0.25% by weight of the attractant extract solution.

FORMULATION EXAMPLE 2

Fly ribbon 100 g of a sticky substance which is a mixture of gum arabic, a vinyl chloride emulsion and castor oil (viscosity controller) were mixed with 10 g of the methanol extract solution obtained in Preparation Example 1, and the resulting mixture was sprayed onto each surface of a paper board (7 cm×70 cm) in an amount of 2 g in total to provide a fly ribbon.

FORMULATION EXAMPLE 3

Dry bait for fly attracting trap 50 g of the methanol extract solution obtained in Preparation Example 1 were added to 100 g of a 10% aqueous solution of an insecticide Azamethiophos diluted 100-fold with water and then 500 g of brown sugar and 500 g of rice bran were added thereto to provide a dry bait for a fly attracting trap.

FORMULATION EXAMPLE 4

Dry bait for fly attracting trap 50 g of the ethanol extract solution obtained in Preparation Example 2 were added to 100g of a 10% aqueous solution of an insecticide Azamethiophos diluted 100-fold with water and then 500 g of brown sugar and 500 g of rice bran were added thereto to provide a dry bait for a fly attracting trap.

We claim:

1. A method of attracting flies of the Muscidae family or the Muscinae family comprising providing in a locus where said flies exist a fly attractant composition extracted from a bamboo with an extractive solvent selected from the group consisting of water and $C_1$-$C_4$ alcohol.

2. The method of attracting flies according to claim 1, wherein said bamboo is a bamboo shoot.

3. The method of attracting flies according to claim 1, wherein said solvent is methanol or ethanol.

4. The method of attracting flies according to claim 1, wherein said bamboo is a bamboo shoot and said solvent is water or a $C_1$-$C_4$ alcohol.

5. The method of attracting flies according to claim 1, wherein said bamboo is a bamboo shoot and said solvent is methanol or ethanol.

6. The method of attracting flies according to claim 4, wherein said fly attractant composition further comprises an insecticide and providing said fly attractant composition by a residual spray method.

7. The method of attracting flies according to claim 6, wherein said composition is used in an amount of 0.01 to 10 w/w % based on said insecticide containing 0.2% by weight of an active insecticidal ingredient.

8. The method of attracting flies according to claim 4, which is the fly attracting trap method.

9. The method of attracting flies according to claim 8, wherein said composition is used in an amount of 0.05 to 10 based on said insecticide containing 0.1% by weight of an active insecticidal ingredient in terms of weight ratio.

10. The method of attracting flies according to claim 1, wherein the flies are selected from the group consisting of *Musca domestica, Fannia canicularis* and *Muscina stabulans.*

11. The method of attracting flies according to claim 10, wherein the bamboo is selected from the group consisting of Graminaae and Bambusoidae.

12. The method of attracting flies according to claim 10, wherein the bamboo is selected from the group consisting of *Phyllostachys heterocycla, Phyllostachys nigra* and *Phyllostachys bambusoides.*

13. The method of attracting flies according to claim 12, wherein the extractive solvent is selected from the group consisting of water, methanol and ethanol and the bamboo is a bamboo shoot.

14. The method of attracting flies according to claim 6, wherein the insecticide is selected from the group consisting of an organophosphate, a pyrethroid and a carbamate.

15. The method of attracting flies according to claim 14, wherein the insecticide is selected from the group consisting of propetamphos, azamethipos, chloropyrifos-methyl, diazinon, trichlorofon, fenitrothion, allethrin, permethrin, chrysron, etofenprox, cabaryl, propoxur and 2-s-butylphenyl N-methylcarbamate.

16. The method of attracting flies according to claim 7, wherein the active insecticide ingredient is selected from the group consisting of propetamphos, azamethipos, chloropyrifos-methyl, diazinon, trichlorofon, fenitrothion, allethrin, permethrin, chrysron, etofenprox, cabaryl, propoxur and 2-s-butylphenyl N-methylcarbamate.

17. The method of attracting flies according to claim 9, wherein the active insecticide ingredient is selected from the group consisting of propetamphos, azamethipos, chloropyrifos-methyl, diazinon, trichlorofon, fenitrothion, allethrin, permethrin, chrysron, etofenprox, cabaryl, propoxur and 2-s-butylphenyl N-methylcarbamate.

* * * * *

UNITED STATES PATENT AND TRADEMARK OFFICE
CERTIFICATE OF CORRECTION

PATENT NO. : 5,356,621
DATED : October 18, 1994
INVENTOR(S) : TABARU et al It is certified that error appears in the above-identified patent and that said Letters Patent is hereby corrected as shown below:

Title Page, [22]: delete "Filed: Feb. 10, 1993" and insert:

-- PCT Filed:     Aug. 29, 1991

[86] PCT No.:     PCT/JP91/01147

§ 371 Date:     Feb. 10, 1993

§ 102(e) Date:     Feb. 10, 1993

[87] PCT Pub. No.:     WO92/03928

PCT Pub. Date:     Mar. 19, 1992 --.

Column 6, line 39, Claim 8: after "is" delete "the", insert --a--.

Signed and Sealed this

Fifth Day of December, 1995

Attest:

BRUCE LEHMAN

*Attesting Officer*      *Commissioner of Patents and Trademarks*